United States Patent
Halvorsen et al.

(10) Patent No.: US 8,425,733 B2
(45) Date of Patent: Apr. 23, 2013

(54) METHOD FOR DEWATERING A MIXTURE OF MOSTLY ETHANOL AND WATER

(75) Inventors: Geir Halvorsen, Stjordal (NO); Kjetil Evenmo, Trondheim (NO); Carl Ivar Gotaas, Trondheim (NO)

(73) Assignee: Epcon Energy and Process Control AS, Trondheim (NO)

( * ) Notice: Subject to any disclaimer, the term of this patent is extended or adjusted under 35 U.S.C. 154(b) by 419 days.

(21) Appl. No.: 12/679,931

(22) PCT Filed: Oct. 9, 2008

(86) PCT No.: PCT/NO2008/000353
§ 371 (c)(1),
(2), (4) Date: Apr. 19, 2010

(87) PCT Pub. No.: WO2009/048335
PCT Pub. Date: Apr. 19, 2009

(65) Prior Publication Data
US 2010/0270139 A1    Oct. 28, 2010

(30) Foreign Application Priority Data
Oct. 12, 2007    (NO) .................................. 20075207

(51) Int. Cl.
*B01D 3/32*    (2006.01)
*B01D 3/14*    (2006.01)
(52) U.S. Cl.
USPC .................... 203/19; 203/21; 203/25; 203/27
(58) Field of Classification Search ................... 203/19, 203/21, 25, 27; 568/917
See application file for complete search history.

(56) References Cited

U.S. PATENT DOCUMENTS

| | | | |
|---|---|---|---|
| 2005/0252377 A1 | 11/2005 | Coan et al. | |
| 2006/0070867 A1* | 4/2006 | Ikeda | 203/25 |
| 2008/0135396 A1* | 6/2008 | Blum | 203/25 |
| 2011/0130598 A1* | 6/2011 | Huang et al. | 568/917 |

FOREIGN PATENT DOCUMENTS
EP    0695574    2/1996

* cited by examiner

*Primary Examiner* — Duane Smith
*Assistant Examiner* — Ives Wu
(74) *Attorney, Agent, or Firm* — Ladas & Parry LLP

(57) ABSTRACT

Method for dewatering a mixture of mostly ethanol and water which is split into a first partial feed flow (3) that is directed to a distillation column (32) as a reflux flow while a second partial feed flow (4) is directed to an evaporator unit (31) as an evaporator inlet flow and leaves the top of the evaporator unit as an evaporator outlet flow (6). A top discharge flow (7) from distillation column (32) is returned and combined with the evaporator outlet flow (6) to a combined flow (8) at an overpressure and which in a compressor unit (33) is compressed to a combined, compressed flow (10) which enters a dewatering unit (34) in which it is split into a water-rich permeate flow (14) and a retentate flow (11) in the form of substantially water free ethanol. The permeate flow (14) is condensed in a condenser (39) at an underpressure whereafter permeate flow (15) is pressurized by a pump (42) to a flow (16) which is fed to distillation column (32), which is supplied with external thermal energy by a heat exchanger (36), and there split into a water rich bottom discharge flow (18) and an ethanol-rich top discharge flow (7). The retentate flow (11) is used an energy source in a retentate heat exchanger (37) of evaporator unit (31) before leaving as a product flow (12).

14 Claims, 2 Drawing Sheets

006## METHOD FOR DEWATERING A MIXTURE OF MOSTLY ETHANOL AND WATER

The present invention concerns a method for dewatering a mixture comprising mostly ethanol and water as defined by the characterizing part of claim 1.

BACKGROUND

Industrially water and ethanol often are present in combinations which are not optimal for further use of any one of these compounds. Ethanol as a raw material is suitable as a solvent for a plurality of processes or as an energy source. As an example combinations of water and ethanol are present in varying ratios in processes which have as an object to provide substantially water free ethanol as an energy source produced from biological raw materials. In this connection the ethanol is typically referred to as bioethanol.

Traditional distillation process is typically used for the manufacture of ethanol with a water content somewhat higher than the azeotropic point of the composition. In order to reduce the water content of the ethanol/water composition further, to thereby enhance the utility of the ethanol and its value as a product, different methods have been attempted as described in the following paragraphs.

Multi-component distillation (also referred to as azeotropic distillation) has been, and still is, used for this purpose. A comparatively high energy consumption and use of chemicals are characteristic features of this technique. There are known process solutions for multi-component distillation in which energy recovery, hereby included mechanical recompression of process steam, is included. Examples are found in JP patent 59196833, FR patent 2855170 and JP patent 60226837, which describe distillation columns operated in cascade in combination with recompression of process steam.

Another method is the so-called extractive distillation. Also this method involves the use of chemicals for the extraction step. U.S. Pat. No. 5,294,304 and JP patent 61254177 describes such processes in which recompression of process steam is included in the total energy system.

Two other techniques are molecular sieve and vapour permeation in which upstream vapour is generated in evaporator or taken directly from a traditional distillation process. Discharge flows in such techniques are a retentate (substantially water-free ethanol) and a permeate containing the water with a larger or smaller portion of ethanol which is typically condensed out and then recovered in distillation column. Traditional processes with evaporator consume energy for the evaporation of the feed liquid and for the recovery of the permeate ethanol portion, inclusive the generation of reflux liquid in the distillation step of said permeate.

US patent 2007000769 describes traditional molecular sieve process without recompression of process vapour. The main difference between molecular sieve and vapour permeation is that with the molecular sieve the dewatering step as such is conducted batch wise, why typically a number of molecular sieve tanks are typically mutually interchanged and the tanks which are not in production are subject to a recovery process. In this manner the process upstream and downstream is operated in a continuous manner and the discharge flows from the dewatering unit of the molecular sieve is a retentate and a permeate like with the vapour permeation.

Membrane separation with the feed in liquid form through the membrane, so-called pervaporation, is also a technique that is used. The discharge permeate flow is also with this technique in form of vapour while the retentate is in liquid phase. The energy consumption is comparatively low in comparison with traditional vapour permeation since there is no need for energy supply to evaporate the retentate portion of the feed. The energy supplied is in stead used to evaporate the permeate and to recover the permeate ethanol portion, also included generation of reflux liquid to the distillation step of said permeate. Pervaporation is a less robust technique with respect to the lifetime of membranes, since the membranes are exposed to possible impurities in the feed. There are known processes involving pervaporation in which mechanical recompression of process vapour is included. As an example JP patent 63059308 describes a process for pervaporation of ethanol. The permeate from the membrane flows via a vapour compression step before being fed to the distillation step as feed vapour. Compression of process vapour in this process has the consequence that the permeate can be maintained as vapour into the distillation column, thereby reducing the energy amount which would else be needed for recovery of ethanol from the permeate.

Another example of recompression of permeate is described in JP patent 5137969, where a pressure increase of the permeate in vapour form is used to condense this at the available cooling water temperature in stead of having to use a cooling medium produced by an energy demanding refrigeration unit.

OBJECTIVES

It is an object of the present invention to provide a low-energy method to separate water from a liquid mixture of mostly ethanol and water.

It is furthermore an object to be able to achieve the first object under industrial conditions, i.e. with a cost-efficient full scale plant having a highest possible operational availability.

THE INVENTION

The above mentioned objects are achieved by the method according to the present invention which is defined by claim 1.

Preferred embodiments of the invention are disclosed by the dependent claims.

Method for dewatering a mixture of mostly ethanol and water, comprising evaporation, distillation, compression, heat exchanging and vapour permeation or molecular sieve, the feed of mostly ethanol and water in liquid phase being split into a first partial feed flow being charged to a distillation column as a reflux flow while another partial feed flow being fed to an evaporator as an evaporator feed flow, leaving the top of the evaporator as an evaporator discharge flow while the upper discharge flow from the distillation column being returned and combined with the evaporator discharge flow to a combined flow at an overpressure which in a mechanical compressor unit is compressed to a compressed combined flow that enters a dewatering unit to be split in a water-rich permeate flow and a substantially water free retentate flow, the permeate flow subsequently being condensed in a condenser at an underpressure generated by a vacuum system and in liquid form being pressurized and charged as a feed flow to the distillation column receiving external thermal energy via a heat exchanger and being split into a bottom discharge flow of substantially water and an ethanol-rich top discharge flow, the retentate flow being used as an energy source in a retentate heat exchanger of the evaporator unit before being discharged as a liquid product flow.

A person skilled in the art will realize that the mixture can, and normally will, contain smaller amounts of components other than ethanol and water, such as for example denaturants and small amounts of fusel oils and heavy alcohols.

According to the present invention it is mandatory to supply external energy only to the distillation column. The process is designed in a manner in which this energy is used fully for evaporation of the feed flow in addition to recovery of the ethanol part of the permeate. The possibility of supplying external energy also to the evaporator is not excluded, but is not mandatory. The driving force of the dewatering unit in vapour permeation is the difference in water vapour pressure between retentate and permeate side, which in practice is achieved by removing the permeate at an underpressure while supplying the feed vapour at an overpressure.

Below the process is described more completely in the form of preferred embodiments and with references to the enclosed drawings.

DETAILED EMBODIMENTS OF THE INVENTION

It should be understood that the exemplification in the form of specific figures below is related to a plant comprising a dewatering unit 34 based on vapour permeation if nothing else is indicated. All indications of relative amounts of process flows are as % by weight unless otherwise specified.

Figure 1:
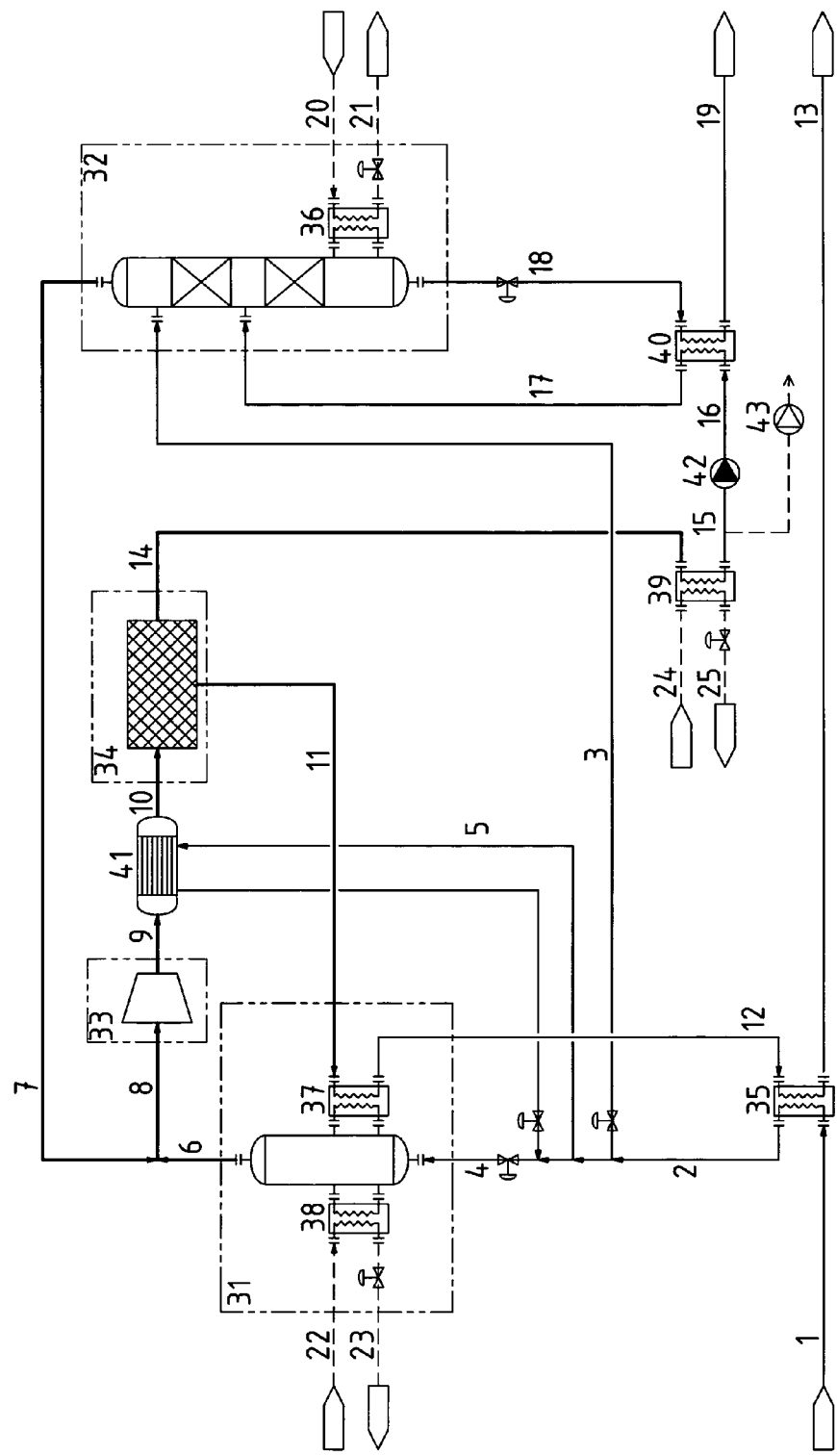
FIG. 1 is a flow chart of a preferred embodiment of the present invention.

FIG. 1 shows how a supplied ethanol rich feed flow 1 is preheated in a heat exchanger 35 to a preheated feed flow 2 and thereafter split into a first partial feed flow 3, a second partial feed flow 4 with an internal flow 5 that is further preheated in heat exchanger 41. First partial feed flow 3 is charged to a distillation column 32 where it enters as a reflux flow while second partial feed flow 4 enters an evaporator unit 31. First partial feed flow 3 normally corresponds to less than 20% of feed flow 1. The evaporator outlet flow 6 from evaporator unit 31 is combined with top discharge flow 7 from distillation column 32. The feed flow 1 typically has an ethanol content of 70% or more and more preferred 80% or more. In cases of dewatering with molecular sieve, corresponding figures are 80% or more and more preferred 90% or more.

The, by process flows 6 and 7, combined flow 8 enters a compressor unit 33 and the thus compressed combined flow 9 enters a gas cooler 41 from which the thus cooled process flow 10, typically having a pressure in the range 2-8 bara (dependent upon dewatering method and also by type of membrane if vapour permeation is used for dewatering), enters a dewatering unit 34 which is typically based on molecular sieve or vapour permeation. A substantially water free retentate flow 11 and a water rich permeate flow 14 are discharged from the dewatering unit 34. The retentate flow 11 typically has up to 2% water. For bioethanol the requirement to the water content in the retentate is <0.3%, which by the present method is obtainable under normal process conditions for the dewatering unit. The compressor unit 33 ensures that the ethanol rich retentate flow is at a higher saturation temperature than the evaporation temperature in evaporator unit 31, so that latent energy in the process flow is utilized in the process by heat exchange in a heat exchanger 37 connected to the evaporator unit 31. The condensed retentate flow 12 from heat exchanger 37 can release further energy in heat exchange with feed flow 1 in heat exchanger 35 as already discussed. A product flow 13 of substantially water free ethanol leaves heat exchanger 35.

The water rich permeate flow 14, typically containing 5-40% ethanol, is condensed in condenser 39 at a underpressure (0 to 1 bara) generated by a vacuum system illustrated by vacuum pump 43, whereafter the liquid permeate flow 15 is pressurized to a pressurized permeate flow 16 and preheated in heat exchanger 40 and then as process flow 17 charged as liquid feed to the distillation column 32. The bottom discharge flow 18 from distillation column 32 releases heat to the pressurized permeate flow 16 in heat exchanger 40 before leaving the process as discharge flow 19 of substantially clean water, typically more than 99% water.

External thermal energy is supplied to the process in connection with distillation column 32 and more specifically by means of heat exchanger 36 connected to same. Additional energy can optionally be supplied in connection with evaporator unit 31 by means of a heat exchanger 38 discussed below. The heat medium 20 and 22 into heat exchanger 36 and heat exchanger 38 respectively, is typically hot liquid or steam.

The lifetime of dewatering unit 34 with respect to vapour permeation is affected by any impurities present in its feed vapour. To avoid an accumulation of undesired volatile components in distillation column 32, like fusel oil, a side outlet (not shown) may be arranged from the column. To avoid accumulation of undesired components such as salts, other solid materials and heavy (high boiling) alcohols in liquid sump of evaporator unit 31, a minor liquid flow (not shown), typically less than 5% of the feed flow 1, is discharged from evaporator unit 31 to process flow 17 or to reflux flow 3 to there be included as a small amount of feed or reflux to distillation column 32 from which the undesired components either leaves with the bottom discharge flow 18 or alternatively leaves via the mentioned side outlet from the column. With the present process the energy consumption will not increase if the above described minor liquid flow is taken from the liquid sump of evaporator unit 31 to distillation column 32.

Figure 2:
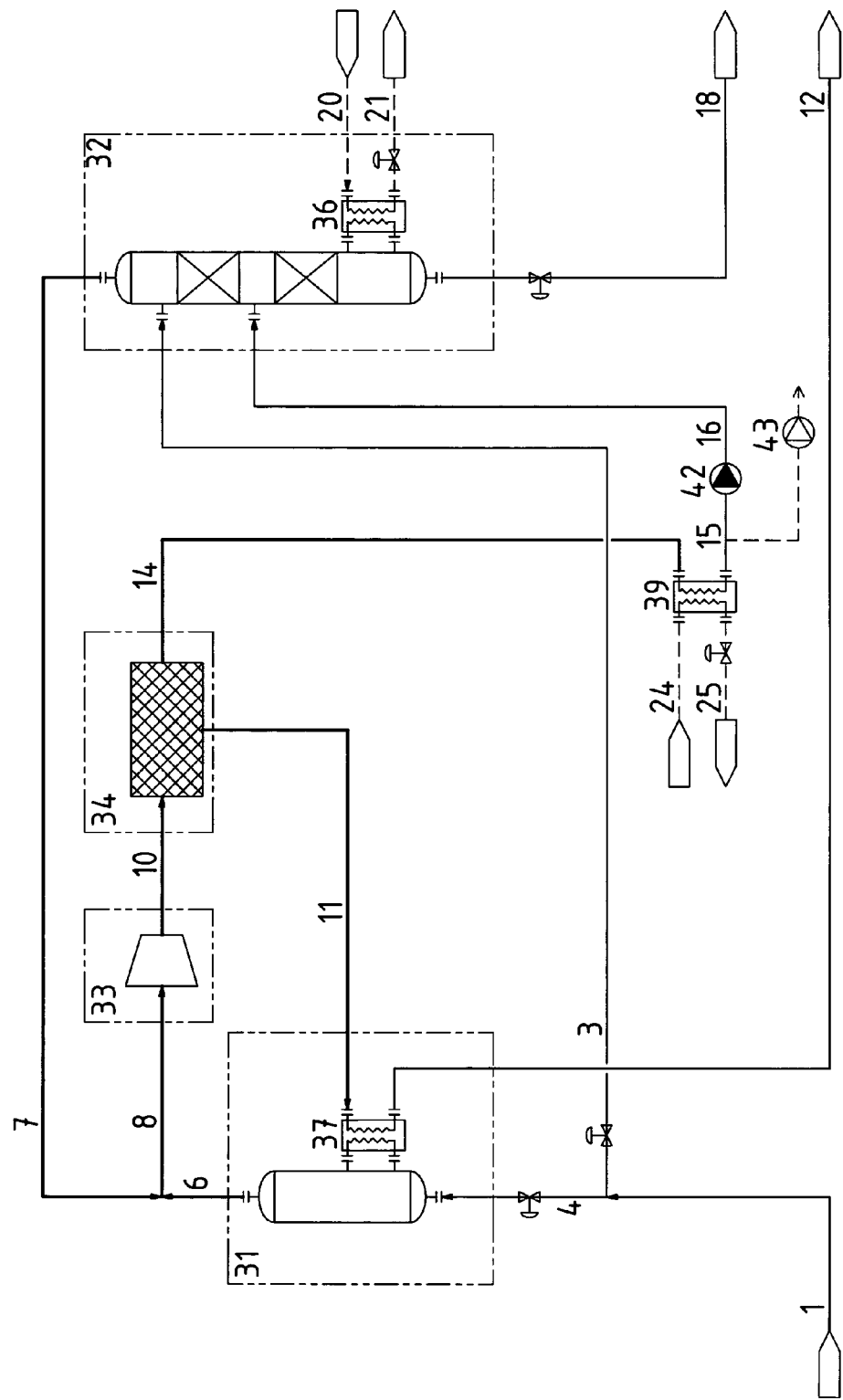
FIG. 2 is a flow chart of a simpler embodiment of the present invention.

FIG. 2 shows a simpler embodiment of the invention than FIG. 1. The differences can simplest be explained by an explanation of what has been left out in FIG. 2, namely the heat exchangers 35, 38, 40, and 41 which would normally be present in a commercial plant, but which are not mandatory to achieve the basic advantages of the present invention. The energy that is recovered in heat exchangers (preheaters) 35 and 40, can, as an example, be used for other purposes. Another example is that feed flow 1 is hot already when entering, and that process flow 12 therefore should exchange heat with other flows or for other purposes.

By comparison of the process flows in FIG. 2 with FIG. 1 it should be observed that process flow 12 in FIG. 2 corresponds to both process flows 12 and 13 in FIG. 1, process flow 16 in FIG. 2 corresponds to both process flows 16 and 17 in FIG. 1, and process flow 18 in FIG. 2 corresponds to both process flows 18 and 19 in FIG. 1.

As mentioned in relation to FIG. 1 feed flow 1 is typically preheated before it is split and shared between distillation column 32 and evaporator unit 31. This preheating preferrably takes place in heat exchange with retentate flow 12 in heat exchanger 35 in FIG. 1.

It is furthermore preferred that the compressor unit 33 is a mechanical vapour compressor. Alternatively the compressor unit may be based on thermal recompression of process vapour by means of a vapour ejector, for which high pressure ethanol vapour is used as drive vapour to the ejector. The alternative will provide a lesser degree of energy recovery.

It is possible, and will often be preferred, that external energy is supplied also to the evaporator unit 31 in addition to the latent energy from the retentate (supplied by heat exchanger 37). This external energy can be supplied in a heat exchanger 38 that receives heating medium 22.

The permeate flow 14 forms basis for an inlet (feed) flow 17 to distillation column 32. The permeate flow 14 is first cooled and condensed at underpressure in one or more heat exchangers as illustrated by heat exchanger 39 and cooling medium 24 and thereafter pressurized by one or more pumps as illustrated by pump 42, to a pressurized permeate flow 16. Underpressure (vacuum) is an important driving force for the water removal which is achieved by a vacuum system illustrated by vacuum pump 43 at the discharge side of heat exchanger 39. It is furthermore preferred, to optimize the energy consumption of the process, to heat exchange the condensed permeate flow 16 against the bottom discharge flow 18 from distillation column 32 before the thus heated permeate flow 17 enters distillation column 32.

Downstream of the evaporator unit 31 the evaporator outlet flow 6 is combined with top discharge flow 7 from distillation column 32 and the combined flow 8 is compressed which leads to overheating of the compressed combined flow 10. It may be preferred to cool this flow before it enters the dewatering unit 34. The cooling may take place e.g. in a heat exchanger 41 with a cooling medium 5 which may be a "branch" of the feed flow to the process, the net supplied heat thus recovered being used another place in the process.

The feed liquid 1 is preheated with sensible heat from the retentate flow 12. The major amount of the feed is evaporated in evaporator unit 31. A smaller amount of the feed is evaporated in the distillation column 32 by being used as a reflux liquid 3. A third fraction 5 of the feed flow 1 can further be preheated in heat exchanger 41 before being directed to evaporator unit 31. Alternatively the process flow 5 is evaporated in compressor unit 33 by directly being added to the compressed, overheated gas flow 9.

A major part of the energy recovery is achieved by mechanical recompression of process vapour in suitable compressor equipment. The drive energy for the compressor equipment can be electric or thermal energy. If thermal energy is used, waste energy from the equipment being used may, wholly or partially, be used as energy supply for the patented process. Most of the energy supplied to an electric motor of the compressor equipment (ca. 90-95%), constitutes the useful energy in the total process.

Calculation Example

Traditional vapour permeation (**) without MVR and with reflux liquid generated internally (*):
  Feed concentration: 85% EtOH in water
  Product capacity: 10.000 kg/h
  Total thermal energy consumption: 3200 kW
  Total electric energy consumption: 25 kW
  Feed concentration: 95% EtOH in water
  Product capacity: 10.000 kg/h
  Total thermal energy consumption: 2400 kW
  Total electric energy consumption: 25 kW The present process in the case of vapour permeation (*)(**):
  Feed concentration: 85% EtOH in water
  Product capacity: 10.000 kg/h
  Total thermal energy consumption: 1150 kW
  Total electric energy consumption: 175 kW
  Feed concentration: 95% EtOH in water
  Product capacity: 10.000 kg/h
  Total thermal energy consumption: 375 kW
  Total electric energy consumption: 175 kW Reduced energy consumption for 85% EtOH in feed=ca. 60%
Reduced energy consumption for 95% EtOH in feed=ca. 80%

(*): Exclusive heat loss and any energy supplied to refrigeration system for the production of cooling medium to condenser.

(**): For molecular sieve the reduction of energy consumption will be less compared to the case of vapour permeation mainly due to the comparatively energy demanding regeneration process.

The invention claimed is:

1. Method for dewatering a mixture of mostly ethanol and water comprising evaporation, distillation, compression, heat exchanging and vapour permeation or molecular sieve, characterized in that the feed flow (1) of mostly ethanol and water is split into a first partial feed flow (3) that is directed to a distillation column (32) as a reflux flow while a second partial feed flow (4) is directed to an evaporator unit (31) as an evaporator inlet flow and leaves the top of the evaporator unit as an evaporator outlet flow (6) while a top discharge flow (7) from distillation column (32) is returned and combined with the evaporator outlet flow (6) to a combined flow (8) at an overpressure and which in a compressor unit (33) is compressed under formation of a combined, compressed flow (10) which enters a dewatering unit (34) in which it is split into a water-rich permeate flow (14) and a retentate flow (11) in the form of substantially water free ethanol, the permeate flow (14) being condensed in a condenser (39) at an underpressure generated by a vacuum system illustrated by vacuum pump (43) whereafter permeate flow (15) is pressurized by a pump (42) to a flow (16) which is fed to distillation column (32), which is supplied with external thermal energy by a heat exchanger (36), and split in a water-rich bottom discharge flow (18) and an ethanol rich top discharge flow (7) while the retentate flow (11) is used as an energy source in a retentate heat exchanger (37) of the evaporator unit (31) before being discharged as a product flow (12).

2. Method as claimed in claim 1, characterized in that feed flow (1) is preheated before it is split and distributed to distillation column (32) and evaporator unit (31).

3. Method as claimed in claim 2, characterized in that the feed flow (1) is preheated in a heat exchanger (35) in heat exchange with product flow (12).

4. Method as claimed in claim 1, characterized in that compressor unit (33) is a mechanical vapour compressor.

5. Method as claimed in claim 1, characterized in that the evaporator unit (31) is supplied with external thermal energy (22) by a heat exchanger (38) in addition to the energy being supplied from the retentate (11) by retentate heat exchanger (37).

6. Method as claimed in claim 1, characterized in that the permeate flow (16) is preheated in a heat exchanger (40) by heat exchange with the bottom discharge flow (18) from distillation column (31) before the former forms a distillation feed flow (17).

7. Method as claimed in claim 1, characterized in that the compressed combined process flow (10) from compressor unit (33) is cooled either directly or indirectly before entering dewatering unit (34).

8. Method as claimed in claim 1, characterized in that the relative amount of ethanol in the feed flow (1) is at least 70%.

9. Method as claimed in claim 1, characterized in that the relative amount of ethanol in the feed flow (1), when the dewatering unit (34) is a molecular sieve, is at least 80%.

10. Method as claimed in claim 1, characterized in that a limited liquid flow is led from the liquid sump of evaporator unit (31) to distillation column (32) via distillation feed (16 or 17) or via reflux flow (3) entering the distillation column.

11. Method as claimed in claim 1, characterized in that the retentate flow (11) typically contains up to 2% water.

12. Method as claimed in claim 8, characterized in that the relative amount of ethanol in the feed flow (1) is at least 80%.

13. Method as claimed in claim 9, characterized in that the relative amount of ethanol in the feed flow (1), when the dewatering unit (34) is a molecular sieve, is at least 90%.

14. Method as claimed in claim 11, characterized in that the retentate flow (11) typically contains up to 0.3% water.

* * * * *